United States Patent [19]
Cox

[11] Patent Number: 5,545,792
[45] Date of Patent: Aug. 13, 1996

[54] ISOMERIZATION CATALYST AND PROCESS

[75] Inventor: William L. Cox, Houston, Tex.

[73] Assignee: Amoco Corporation, Chicago, Ill.

[21] Appl. No.: 342,509

[22] Filed: Nov. 21, 1994

[51] Int. Cl.[6] ................................................ C07C 5/25
[52] U.S. Cl. ........................ 585/665; 585/670; 502/170
[58] Field of Search .............................. 585/665, 670; 502/103, 156, 170

[56] References Cited

U.S. PATENT DOCUMENTS

| | | | |
|---|---|---|---|
| 3,409,681 | 11/1968 | Kroll | 260/666 |
| 4,587,374 | 5/1986 | Peters | 585/670 |
| 5,430,165 | 7/1995 | Cox et al. | 556/190 |

FOREIGN PATENT DOCUMENTS 1329140  9/1973  United Kingdom.

Primary Examiner—Shrive Beck
Assistant Examiner—Timothy H. Meeks
Attorney, Agent, or Firm—Stephen L. Hensley

[57] ABSTRACT

A process for producing an internal olefin of the formula

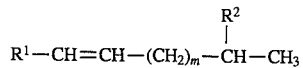

where $R^1$ and $R^2$ are the same or different and are either a hydrogen or an alkyl and m is an integer of from 0 to 20 comprising contacting a vinyl or vinylidene olefin of the formula

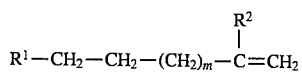

where $R^1$, $R^2$ and m are as previously defined, with a catalytically effective amount of a mixture of i) an aluminum compound of the formula $R^3{}_n Al(OR^4)_p$ where $R^3$ and $R^4$ are the same or different and are alkyl, n is an integer from 0.75 to 2.25, and p is an integer from 0.75 to 2.25, the sum of n and p being 3, and ii) a cobalt (II) salt of an organic carboxylic acid, at a temperature of from about 25° C. to about 250° C. whereby a major amount of said internal olefin is produced and only a minor amount of a tri-substituted internal olefin.

15 Claims, No Drawings

ISOMERIZATION CATALYST AND PROCESS

FIELD OF THE INVENTION

This invention relates to a catalyst mixture and the use of such catalyst mixture in the isomerization of alpha-olefins. More particularly, this invention relates to a novel catalyst mixture prepared by admixing an alkyl-aluminum alkoxide and a cobalt salt of an organic carboxylic acid.

BACKGROUND OF THE INVENTION

Organoaluminum compounds have been previously utilized in the preparation of catalysts such as Ziegler-type catalysts. These catalysts preparations are based on the ability of organoaluminum compounds to act as reducing agents, i.e., reducing a transition metal to the zero valence state, e.g., U.S. Pat. No. 3,113,986.

U.S. Pat. No. 2,959,607 discloses the preparation of aluminum alkyls which contain at least one n-octyl group by subjecting octene-2 to the action of at least a stoichiometric amount of triisobutyl aluminum in the presence of a cobalt chloride catalyst at substantially atmospheric pressure. The catalyst apparently acts as both an isomerization and displacement catalyst in this process. The aluminum alkyls can be oxidized and hydrolyzed to make octanol-1.

U.S. Pat. No. 2,962,513 discloses a process for forming longer chain aluminum alkyls by a catalyzed olefin displacement of ethylene from ethyl aluminum compounds using a 100 to 300 percent stoichiometric excess of $C_3$ or higher alpha-olefins. The process uses salts and oxides of Group VIII metal as catalysts at temperatures of from about 50° to 200° C. at atmospheric pressure. Ethylene is evolved in the reaction.

U.S. Pat. No. 3,784,623 discloses the control of the increased tendency of the alpha-olefins to isomerize to internal olefins, which tendency is associated with catalytic displacement, by adding inhibitors or catalyst inactivators to the process.

U.S. Pat. No. 3,439,054 discloses a carbonyl catalyst that is useful for both hydrogenation of various unsaturated compounds as well as for causing isomerization in such compounds. The catalyst is dissolved as a mixture of transition metal carbonyl and an organoaluminum compound. This patent notes that organoaluminum compounds, such as alkoxides or halides, do not produce an active catalyst when used with the transition metal complex disclosed therein.

BRIEF SUMMARY

In accordance with this invention, there is provided a catalyst that is a mixture of i) an alkyl aluminum alkoxide of the formula $R^3{}_nAl(OR^4)_p$, where $R^3$ and $R^4$ are alkyl and n is an integer from 0.75 to 2.25, p is an integer from 0.75 to 2.25 and the sum of n and p is 3, and ii) a cobalt salt of an organic carboxylic acid.

The catalyst is useful in a process for preparing internal olefins of the formula $$R^1-CH=CH-(CH_2)_m-CH-CH_3$$
$$\overset{|}{R^2}$$

where $R^1$ and $R^2$ are the same or different and are hydrogen or alkyl and m is an integer from 0 to 20 from vinyl olefins of the formula $$R^1-CH_2-CH_2-(CH_2)_m-\overset{\overset{R^2}{|}}{C}=CH_2$$

where $R^1$, $R^2$ and m are as previously defined.

The internal olefins are useful when oligomerized as oils. Depending on their viscosity, different applications for such oils are known, e.g., as lubricants. These materials are mixtures of different percentages of dimer, trimer, tetramer, pentamer and higher oligomers which oligomers are produced in different proportions in the oligomerization process. In order to increase the viscosity, processes are used which either produce more of the higher oligomers or some of the lower oligomers are removed such as by distillation. Most low viscosity dimer and trimer products are obtained as by-products of the production of higher viscosity synthetic oils. Due to the increasing use of dimers in applications such as low temperature lubricants and drilling fluids, methods for their preferential production are of interest.

DETAILED DESCRIPTION

The olefins used in making the internal olefin are predominately (at least 50 mole percent) $C_6$ to $C_{20}$ straight- or branched-chain monoolefinically unsaturated hydrocarbons in which the olefinic unsaturation occurs at the 1- or alpha-position of the carbon chain. Typically they have the following formula $$R^1-CH_2-CH_2-(CH_2)_m-\overset{\overset{R^2}{|}}{C}=CH_2 \quad \text{Formula I}$$

where $R^1$ and $R^2$ are the same or different and are hydrogen or alkyl, i.e, $C_1$ to $C_{20}$ linear or branched alkyl, preferably $C_1$ to $C_6$ linear or branched alkyl, most preferably $C_1$ to $C_4$ linear or branched alkyl, e.g. methyl, ethyl and the like, and m is an integer from 0 to 20. Particularly preferred are components where $R_1$ is alkyl and $R_2$ is hydrogen.

Such alpha-olefins are commercially available and can be made by the thermal cracking of paraffinic hydrocarbons or by the well-known Ziegler ethylene chain growth and displacement on triethyl aluminum. Individual olefins may be used as well as mixtures of such olefins. Examples of such olefins are 1-hexene, 1-heptene, 1-octene, 1-nonene, 1-decene, 1-dodecene, 1-hexadecene and 1-tetra-decene. The more preferred normal-alpha.-olefin monomers are those containing about 8–12 carbon atoms. The most preferred olefin monomer is 1-decene.

The olefin monomers can also contain minor amounts of up to about 50 and usually less than 25 mole percent of internal olefins and vinylidene olefins. Typically above 70% of said olefin monomers is 1-decene.

The alpha-olefin of Formula I is contacted with a catalytically effective amount of a catalyst mixture comprising an alkyl aluminum alkoxide and a cobalt, (II) salt of an organic carboxylic acid.

The alkyl aluminum alkoxide portion of the catalyst has the formula $R^3{}_nAl(OR^4)_p$ where $R^3$ and $R^4$ arc alkyl as defined above and n is an integer from 0.75 to 2.25, p is an integer from 0.75 to 2.25 and sum of n and p is 3. Thus, the alkyl aluminum alkoxide can be a 1:1 mixture of $R^3Al(OR^4)_2$ and $(R^3)_2AlOR^4$, or the compound $R^3Al(OR^4)_2$ can predominate, e.g., it can be about 95% of said mixture or it can be a minor amount in said mixture, e.g., it can be about 5%. Thus the ratio of $R^3Al(OR^4)_2$ to $(R^3)_2AlOR^4$ can be from about 9.5:05 to about 05:9.5. Preferably, about 30% to about 60% of said mixture is $(R^3)_2AlOR^4$.

The alkyl aluminum alkoxide is readily formed by processes well known to those skilled in the art, i.e., by controlled oxidation of aluminum alkyl.

The catalyst mixture in accordance with the present invention, in addition to the alkyl aluminum alkoxide utilizes as a cocatalyst a cobalt (II) salt. Suitable cobalt salts include, but are not intended to be limited to cobalt acetylacetonate, and preferably, the organic carboxylic acid salts such as the cobalt carboxylates, i.e., cobalt naphthenate, cobalt acetate, cobalt tallate, cobalt stearate, cobalt 2-ethyl-hexanoate, and the like.

The amount of cobalt salt used as the cocatalyst is relatively small and, based on the vinyl olefin, is about 0.001 to about 0.10%, preferably about 0.001 to about 0.005%, most preferably about 0.001 to about 0.003%.

The aluminum alkoxide, present with the vinyl olefin at the time of isomerization is (based on the amount of olefin) from about 0.1% to about 10% by weight. Catalyst concentrations higher than 10% may be used, if desired, but offer no particular advantage over lesser concentrations. For a typical isomerization reaction as contemplated by the present invention, alkoxide concentrations within the range of 0.5 to about 2.0% by weight of the vinyl olefins are preferred.

The isomerization reaction is conducted in a sealed vessel without air at a temperature that is not as low as to retard reaction but not too high such that catalyst activity is diminished due to catalyst decomposition. Thus temperatures in the range of 100° C. to 250° C. have been found conducive to the isomerization reaction, with a range of 150° C. to 200° C. being preferred and 160° C. to 180° C. being most preferred.

The i) cobalt (II) salt of an organic carboxylic acid, and ii) alkyl aluminum alkoxide admixture that is the catalyst of this invention is typically preformed and added to the reaction mixture as such or it may be formed in situ. Thus, for example, to a mixture of the cobalt (II) compound optionally in a suitable inert solvent, an alkyl aluminum alkoxide compound, optionally also in an inert solvent, may be added. The resulting mixture may then be added to the vinyl olefin to accomplish the present isomerization.

It is also possible to first add the alkyl aluminum alkoxide precursor, i.e., the trialkylaluminum to the olefin reaction mass having the cobalt (II) salt already present. After passing oxygen or air into this mass (by sparging for example) for a time suitable to convert the trialkylaluminum into the catalytically active alkyl aluminum alkoxide species (as described herein) the mixture is heated and isomerization effected. It should be noted that the cobalt (II) compound need not be present when such in situ oxidation is carried out but can be added prior to heating and isomerizing. Also the alkoxide can be formed using the oxygen atoms present in the cobalt catalyst.

The most preferred embodiment of the invention is a process for isomerizing a mixture of olefins containing about 10–20 carbon atoms consisting mainly of vinyl olefins and vinylidene olefins and a minor amount of internal olefins. The process comprises heating the mixture of olefins in contact with a catalytic amount of a mixture of i) an alkyl aluminum alkoxide mixture of the compound of the formula $(R^3)_2Al(OR^4)$ and $R^3Al(OR^4)_2$, and ii) a cobalt (II) salt of an organic carboxylic acid at a temperature of about 160° C. to 180° C. until a substantial amount of the vinyl olefins have isomerized to form isomerized internal olefins. The process is characterized in that the isomerized internal olefins formed from the vinyl olefins are mainly internal olefins containing 8–24 carbon atoms having the structure

and only a minor amount of tri-substituted internal olefins having the structure

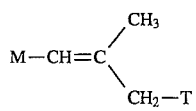

wherein X, Y, M and T are aliphatic hydrocarbon groups such that X plus Y contain about 6–22 carbon atoms and M plus T contain about 4–20 carbon atoms.

EXAMPLE 1

The following example illustrates vinyl olefin isomerization produced by the addition of aluminum alkoxide and a cobalt carboxylate:

(1) A reaction apparatus is set up consisting of a 1000 mL creased flask, agitator, heating mantle, thermometer and nitrogen purge on the vapor space of the flask.

(2) To the flask is added 500 g of olefins having the following analysis:

| G.C. Analysis | | NMR Analysis | |
|---|---|---|---|
| Component | Wt. % | Component | Mole % |
| C14 Olefin | 0.81 | Vinyl | 58.69 |
| C16 Olefin | 48.89 | Branched | 34.39 |
| C18 Olefin | 41.64 | Internal | 6.92 |
| C20 Olefin | 8.66 | Trisub | 0.0 |

(3) To the olefins is added 12.78 g of a mixed ($C_2$–$C_{20}$) aluminum alkoxide having a molar % oxidation of 60%.

(4) The reactants are heated to 170° C. and 30 ppm cobalt is added in the form of cobalt 2-ethyl-hexanoate.

(5) The reactants are maintained at 170° C. for 15 minutes and then cooled to room temperature.

(6) The reaction product is next flashed distilled in a 5-tray Oldershaw column at 5 mmHg vacuum to recover 471.5 g of catalyst free product having the following NMR analysis:

| NMR Analysis | |
|---|---|
| Component | Mole % |
| Vinyl | 1.7 |
| Branched | 20.6 |
| Internal | 68.2 |
| Trisub | 9.4 |

EXAMPLE 2

The following example illustrates vinyl olefin isomerization produced by the addition of a cobalt carboxylate and an aluminum alkyl. The alkoxide is formed in situ by oxidation of the aluminum alkyl with the oxygen present in the cobalt salt.

(1) A reaction apparatus is set up as described in Example 1.

(2) To the reaction flask is added 500 g of olefins having the same composition as in Example 1.

(3) The olefins are heated to 170° C. and 1.5 g of mixed ($C_2$–$C_{20}$) aluminum alkyls having an aluminum concentration of 7 wt. % are added.

(4) To the reactants is added 40 ppm of cobalt in the form of cobalt 2-ethyl-hexanoate.

(5) The reactants are maintained at 170° C. for 15 minutes and then cooled to room temperature.

(6) The reaction product is then flash distilled as described in Example 1 to recover 432.2 g of catalyst free product having the following NMR analysis:

| NMR Analysis | |
|---|---|
| Component | Mole % |
| Vinyl | 1.1 |
| Branched | 15.0 |
| Internal | 68.7 |
| Trisub | 15.2 |

EXAMPLE 3

The following example illustrates that vinyl olefin isomerization does not occur when a fully oxidized (98%) aluminum alkyl is used with cobalt catalyst.

(1) A reaction apparatus is set up consisting of a 100 ml flask, agitator, heating mantle, thermometer and nitrogen purge on the vapor space of the flask.

(2) To the flask is added 30 g of $C_{14}$ olefin having the following NMR analysis:

| NMR Analysis | |
|---|---|
| Component | Mole % |
| Vinyl | 80.51 |
| Branched | 14.57 |
| Internal | 4.92 |
| Trisub | 0.0 |

(3) To the olefin is added 0.50 g of a $C_8$ alkoxide having a molar % oxidation of 98%.

(4) The reactants are heated to 175° C. and 30 ppm cobalt is added in the form of cobalt 2-ethyl-hexanoate.

(5) The reactants are maintained at 180° C. for 15 minutes and then cooled to room temperature.

(6) A 2 ml sample of the reaction product is hydrolyzed with 3 ml of 10% HCl to remove catalyst and a NMR analysis of the organic phase showed the composition to be identical with the starting olefin.

EXAMPLE 4

The following example illustrates that vinyl olefin isomerization with an excess of aluminum alkyl (very low oxidation level) produces a low conversion to internal olefin.

(1) A reaction apparatus is set up as described in Example 3.

(2) To the reaction flask is added 30 g of $C_{14}$ olefin having the same composition as in Example 3.

(3) The olefin is heated to 170° C. and 0.452 g of mixed ($C_2$–$C_{20}$) aluminum alkyls having an aluminum concentration of 7 wt. % are added.

(4) To the reactants is added 45 ppm of cobalt in the form of cobalt 2-ethyl-hexanoate.

(5) The reactants are maintained at 170° C. for 30 minutes and then cooled to room temperature.

(6) A 2 ml sample of the reaction product is hydrolyzed with 3 ml of 10% HCl to remove catalyst and a NMR of the organic phase gave the following:

| NMR Analysis | |
|---|---|
| Component | Mole % |
| Vinyl | 59.72 |
| Branched | 15.91 |
| Internal | 24.36 |
| Trisub | 0.00 |

Only about 26% of the vinyl olefin was isomerized to internal olefins.

What is claimed is:

1. A process for producing an internal olefin of the formula

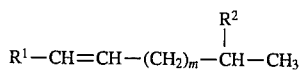

where $R^1$ is alkyl and $R^2$ is either a hydrogen atom or an alkyl and m is an integer of from 0 to 20 comprising contacting at a temperature of from about 100° C. to about 250° C., a vinyl or vinylidene olefin of the formula

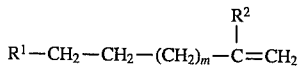

where $R^1$, $R^2$ and m are as previously defined, with a catalytically effective amount of a catalyst mixture formed by controlled oxidation of aluminum trialkyl in an inert atmosphere in the presence of a cobalt salt of an organic carboxylic acid so that the aluminum trialkyl is converted by oxygen from the cobalt salt into an aluminum compound of the formula $R^3{}_n Al(OR^4)_p$ where $R^3$ and $R^4$ are the same or different and are $C_2$–$C_{20}$ alkyl, n is an integer from 0.75 to 2.25, and p is an integer from 0.75 to 2.25, the sum of n and p being 3, to produce said internal olefin.

2. A process of claim 1 wherein $R^1$ and $R^2$ contain about 1–20 carbon atoms such that the total number of carbon atoms in said vinylidene olefin is about 8–24.

3. A process of claim 1 wherein $R^2$ is a hydrogen atom.

4. A process of claim 1 wherein said temperature is about 150° C. to 200° C.

5. A process for isomerizing a mixture of olefins containing about 8–24 carbon atoms, said mixture of olefins comprising 50 to 95 weight percent of vinyl olefins and 5 to 50 weight percent of vinylidene olefins, said process comprising heating said mixture of olefins while in contact with a catalytic amount of a catalyst mixture formed by controlled oxidation of aluminum trialkyl in an inert atmosphere and in the presence of a cobalt (II) salt of an organic carboxylic acid so that the aluminum trialkyl is converted into an aluminum compound of the formula $R^3{}_n Al(OR^4)p$ where $R^3$ and $R^4$ are the same or different and are alkyl, n is an integer from 0.75 to 2.25, and p is an integer from 0.75 to 2.25, the sum of n and p being 3, said controlled oxidation being performed in situ using oxygen present in the cobalt salt, said heating of said mixture of olefins being conducted at a temperature of about 160° C. to 180° C. to effect isomerization of vinyl olefin to internal olefin.

6. A process of claim 5 further characterized in that at least 70 weight percent of the vinyl olefins in said mixture of olefins is decene.

7. The process according to claim 1 wherein said aluminum compound is produced by adding said aluminum trialkyl and said cobalt salt to said olefin and conducting said controlled oxidation in situ.

8. The process according to claim 7 wherein said aluminum compound is 1:1 mixture compounds of the formulas $R^3Al(OR^4)_2$ and $(R^3)_2AlOR^4$.

9. The process according to claim 8 wherein said cobalt salt is a cobalt (II) salt.

10. The process according to claim 9 wherein said cobalt salt is cobalt naphthenate.

11. The process according to claim 1 wherein said aluminum trialkyl has from 2 to 20 carbon atoms in each alkyl group.

12. The process according to claim 11 wherein $R^2$ is a hydrogen atom.

13. The process according to claim 11 wherein said temperature is in the range of 150° C to 200° C.

14. The process according to claim 13 wherein said aluminum compound is produced by adding said aluminum trialkyl and said cobalt salt to said mixture of olefins and conducting said controlled oxidation in situ.

15. The process according to claim 14 wherein $R^2$ is a hydrogen atom.

* * * * *